(12) United States Patent
Mueller

(10) Patent No.: US 6,179,771 B1
(45) Date of Patent: Jan. 30, 2001

(54) COIL ARRANGEMENT FOR TRANSCRANIAL MAGNETIC STIMULATION

(75) Inventor: Edgar Mueller, Heroldsbach (DE)

(73) Assignee: Siemens Aktiengesellschaft, Munich (DE)

(*) Notice: Under 35 U.S.C. 154(b), the term of this patent shall be extended for 0 days.

(21) Appl. No.: 09/296,026

(22) Filed: Apr. 21, 1999

(30) Foreign Application Priority Data

Apr. 21, 1998 (DE) .............................................. 198 17 753
Mar. 31, 1999 (DE) .............................................. 199 14 762

(51) Int. Cl.⁷ ........................................................ A61N 1/00
(52) U.S. Cl. ............................................ 600/13; 600/411
(58) Field of Search ................................ 600/13, 74, 15, 600/11, 411, 421, 422

(56) References Cited

U.S. PATENT DOCUMENTS

| 435,343 | * | 8/1890 | Brown | ................................. | 600/13 |
| 1,164,356 | * | 12/1915 | Kaiser | ................................. | 600/13 |
| 3,658,051 | * | 4/1972 | MacLean | ............................. | 600/14 |
| 5,284,144 | | 2/1994 | Delannoy et al. . | | |
| 5,595,564 | * | 1/1997 | Pina | .................................... | 600/15 |
| 6,029,082 | * | 2/2000 | Srinivasan et al. | ................. | 600/422 |

FOREIGN PATENT DOCUMENTS

| 0 148 566 | 7/1985 | (EP) . |
| 0 655 261 | 5/1995 | (EP) . |
| 0 709 115 | 5/1996 | (EP) . |

OTHER PUBLICATIONS

Transcranial Magnetic Stimulation during Positron Emission Tomography: A New Method for Studying Connectivity of the Human Cerebral Cortex, Paus et al., The Journal of Neuroscience, May 1, 1997, 17 (9): 31 pp. 3178–3184.

* cited by examiner

*Primary Examiner*—Max Hindenburg
*Assistant Examiner*—Brian Szmal
(74) *Attorney, Agent, or Firm*—Schiff Hardin & Waite

(57) ABSTRACT

A coil arrangement for transcranial magnetic stimulation has several individual coils, each having separate current terminals, connected with a support element. The individual coils are constructed in a unitary structural component with a radio-frequency head antenna.

5 Claims, 1 Drawing Sheet

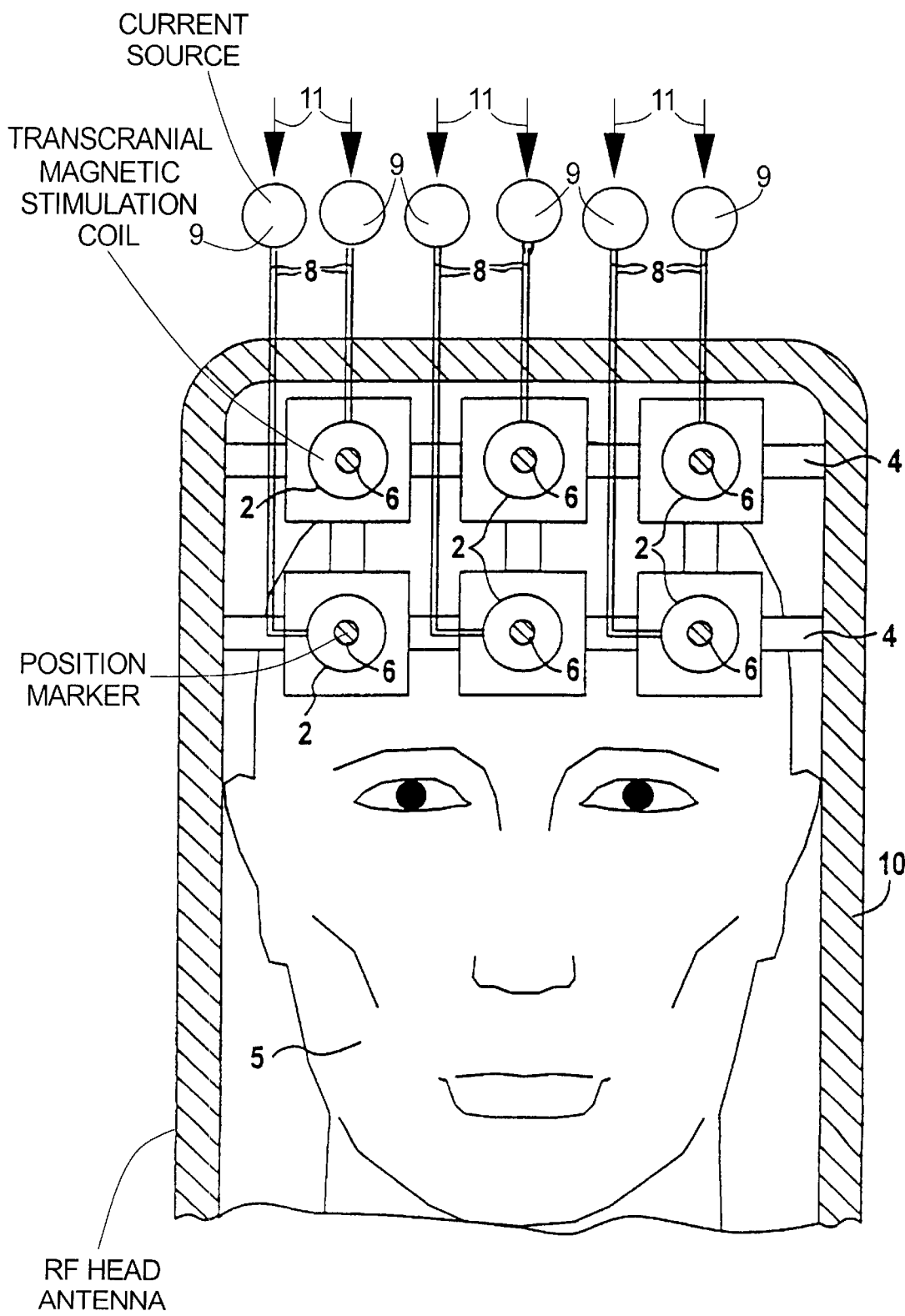

COIL ARRANGEMENT FOR TRANSCRANIAL MAGNETIC STIMULATION

BACKGROUND OF THE INVENTION

1. Field of the Invention

The invention relates to a coil arrangement for transcranial magnetic stimulation of the type having several individual coils with respective individual current terminals, the coils being mounted in a support element.

2. Description of the Prior Art

In the article by Tomas Paus, Robert Jech, Christopher J. Thompson, Roch Comeau, Terry Peters and Alan C. Evans entitled "Transcranial Magnetic Stimulation during Positron Emission Tomography: A New Method for Studying Connectivity of the Human Cerebral Cortex," which appeared in The Journal of Neuroscience, May 1, 1997, vol. 17, no. 9, pp. 3178–3184, a method is specified that enables a mapping of neuronal connections in the brain. By means of transcranial magnetic stimulation (TMS), a neural activity is triggered at a limited location of the brain surface whose function is known. A small coil with a figure-8 conductor configuration is placed at the location of interest—e.g., somewhat above the scalp in the region of the frontal eye area—and a sequence of short magnetic pulses with a magnitude of approximately 1.5 Tesla is applied by feeding in current pulses into the coil. Subsequently, the neuronal response of the brain at other locations is acquired using an imaging method, e.g. by positron emission tomography (PET). If the location of stimulation is the region of the frontal eye area, the response to this stimulation is acquired at the primary visual cortex using PET. In this way, findings concerning the spatial and temporal interconnectedness of brain functions (connectivity) can be obtained.

The TMS coil arrangement specified in this article must be positioned at the desired location. If the stimulation location is to be modified, this requires a new positioning by attending personnel. Due to the time-consuming and thus expensive activity which is necessary given a variation of the location of stimulation, the clinical possibilities for using this known arrangement. Moreover, since the field distribution of the magnetic field is predetermined by the geometry of the coil, additional TMS coil arrangements must be provided if a stimulation with other field profiles is to take place. In addition, the method has only limited availability, due to the imaging by means of PET.

In European Application 0 655 261, an apparatus is specified that is applied externally to the surface of the head as a treatment for delaying the falling out of hair and stimulating hair growth. Several generator elements for the production of electromagnetic waves are arranged on a helmet-like or hat-like components. The effective frequency range is between 10 Hz and 100 Hz and the effective intensity range is between 1 Gauss and 100 Gauss (1 Gauss=0.1 mT). The generator elements are connected with a power generator via respective separate lines.

From European Application 0 148 566, a helmet-like head antenna for magnetic resonance examinations is known. The head antenna is formed by at least one radio-frequency coil that is shaped convexly and/or concavely. The head antenna can thereby be adapted closely to the body part to be examined.

Another arrangement of the type described above is known from European Application 0 709 115. Several coils are arranged on a helmet-like support element. The coils themselves can be driven individually.

U.S. Pat. No. 5,284,144 specifies a combination of a hyperthermia apparatus with a magnetic resonance antenna. The temperature of the heated tissue is monitored via the magnetic resonance antenna. With a connected control unit, the hyperthermia apparatus is controlled so that a predetermined temperature is held constant in the tissue.

SUMMARY OF THE INVENTION

An object of the present invention is to provide a coil arrangement for transcranial magnetic stimulation that avoids the disadvantages of the known TMS coil arrangements and that is more flexible and time-efficient in application.

The above object is achieved in accordance with the principles of the present invention in a coil arrangement for transcranial magnetic stimulation wherein the individual coils, employed for transcranial magnetic stimulation, are mounted in a unitary structural unit together with a radio-frequency head antenna.

Advantages of the inventive combination include, first, the ability to individually drive the respective coils, thereby allowing arbitrary profiling of the magnetic field. Thus, for example, by means of opposite excitation of adjacent coils a figure-8-shaped coil arrangement can be reproduced. At the same time, it is possible, without having to reposition the coil arrangement itself, to trigger a magnetic stimulation at various locations on the surface of the brain by means of corresponding activation of adjacent individual coils. In addition, the structural unity of the individual coils with the radio-frequency head antenna achieves a high signal-to-noise ratio during a (functional) magnetic resonance imaging, while still producing the desired coupling of the magnetic fields produced by the individual coils to the location of stimulation. Local coupling-in of radio-frequency fields during the magnetic resonance imaging procedure is avoided by means of known decoupling measures.

In one embodiment the support element is of rigid construction. A fixed geometrical allocation of the individual coils is thereby set, and in addition the forces that act on the coil conductors due to the high magnetic fields can be intercepted.

A position marker can be allocated to each individual coil, this marker comprising an imaging substance. In the corresponding imaging method, the position markers produce a visible mark in the image, and thus enable identification and location of the stimulating individual coils.

The marker substance can be of a type detectable by means of magnetic resonance technology. With the use of functional magnetic resonance imaging (fMRI) as an imaging method, it is thereby also possible to represent the position of the individual coils.

DESCRIPTION OF THE DRAWINGS

The single FIGURE is a schematic illustration, partly in section, of a coil arrangement for transcranial magnetic stimulation constructed in accordance with the principles of the present invention.

DESCRIPTION OF THE PREFERRED EMBODIMENTS

The FIGURE schematically shows, in a front view, a coil arrangement for transcranial magnetic stimulation with several individual coils 2. The individual coils 2 are arranged on a support element 4, here a pot-shaped or helmet-like rigid frame made of a material that is electrically non-conductive and non-magnetic and which has sufficient strength to retain its shape. During application, the support element 4 with the individual coils 2 is placed on the head 5 in the manner of a helmet. For clarity, only the individual coils 2 arranged on the front side of the support element 4 are shown, but further individual coils 2 are present at the side, rear, and top, so that in principle all regions of the brain can be magnetically stimulated once the support element 4 with the individual coils 2 has been positioned.

In the center of each individual coil 2 there is a position marker 6. The position markers 6 are filled with a substance that can be detected by magnetic resonance technology, such as e.g. salt water, copper chloride or copper nitrate. The position markers 6 produce corresponding marks in the magnetic resonance image, which enable an unambiguous correlation of the activated individual coil 2 with the coordinates of the recorded brain obtained in the magnetic resonance imaging.

Each individual coil 2 has separate current terminals 8 that are connected with corresponding current sources 9 in order to produce the desired low-frequency magnetic fields. One or also several individual coils 2 can be simultaneously activated (symbolized by arrows 11), also with various high currents.

The support element 4 with the individual coils 2 and the position markers 6 is arranged inside a head antenna 10 that is fashioned for transmission and reception of magnetic resonance signals. Many head antennas are known from the prior art, so that only a schematic representation in section is given, and it is not necessary to describe the antenna 10 into detail. Various structural forms are known for the various possible directions of the main magnetic field in the magnetic resonance apparatus.

Decoupling of the individual coils 2 from the transmission antenna of the magnetic resonance apparatus, which can also be the head antenna 10, is accomplished for example by separation of the individual coils 2 from the current supplies, so that the individual coils 2 then represent in principle open conductor loops. The radio-frequency fields required for the magnetic resonance imaging thus cannot induce any currents in the individual coils 2. If current circuits which resonate at the operational frequency of the magnetic resonance apparatus arise within the individual coils 2 due to capacitive or inductive partial couplings, then, by connection of corresponding capacitances, these resonant points can be displaced into regions that are no longer disturbing for the magnetic resonance imaging.

Although modifications and changes may be suggested by those skilled in the art, it is the intention of the inventor to embody within the patent warranted hereon all changes and modifications as reasonably and properly come within the scope of his contribution to the art.

I claim as my invention:

1. A coil arrangement for transcranial magnetic stimulation comprising:

a plurality of individual transcranial magnetic stimulation coils, each of said coils having separate current terminals connected thereto;

a radio-frequency head antenna for magnetic resonance imaging; and a single, unitary structural support element, composed of electrically non-conductive and non-magnetic material, on which all of said coils are mounted together with said radio-frequency head antenna.

2. A coil arrangement as claimed in claim 1 wherein said support element has a helmet-like configuration adapted to be worn on a head of an examination subject.

3. A coil arrangement as claimed in claim 1 wherein said support element is comprised of rigid material.

4. A coil arrangement as claimed in claim 1 wherein each of said individual coils has a position marker allocated thereto identifying a position of the allocated individual coil, the position marker comprising a substance visible in a selected medical imaging technology.

5. A coil arrangement as claimed in claim 4 wherein said substance comprises a substance detectable by magnetic resonance imaging technology.

* * * * *